United States Patent [19]

Hurnik et al.

[11] Patent Number: 5,474,085

[45] Date of Patent: Dec. 12, 1995

[54] REMOTE THERMOGRAPHIC SENSING OF LIVESTOCK

[75] Inventors: Daniel Hurnik; William P. Ireland; Barry W. Stahlbaum; Wendell E. Dawson, all of Prince Edward Island, Canada

[73] Assignee: University of Prince Edward Island, Charlottetown, Canada

[21] Appl. No.: 201,168

[22] Filed: Feb. 24, 1994

[51] Int. Cl.$^6$ ........................................ A61B 5/103
[52] U.S. Cl. .............................. 128/774; 119/174
[58] Field of Search ........................... 128/736, 774, 128/779; 119/174; 250/316.1; 358/108

[56] References Cited

U.S. PATENT DOCUMENTS

| | | | |
|---|---|---|---|
| 3,738,320 | 6/1973 | Holm | 119/14.03 |
| 4,617,876 | 11/1984 | Hayes | 119/155 |
| 4,679,077 | 7/1987 | Yuasa et al. | 358/108 |
| 4,691,712 | 8/1987 | Brown | 128/736 |
| 4,737,847 | 12/1988 | Araki et al. | 358/108 |
| 4,866,276 | 12/1989 | Leavers et al. | 250/341 |
| 4,917,048 | 4/1990 | Beattie et al. | 119/20 |
| 4,917,117 | 4/1990 | Brom et al. | 128/782 |
| 5,009,191 | 4/1991 | Joergensen et al. | 119/20 |
| 5,056,525 | 10/1991 | Hafezi | 128/664 |
| 5,059,796 | 10/1991 | Nakumura | 250/330 |
| 5,121,201 | 6/1992 | Seki | 358/108 |
| 5,163,094 | 11/1992 | Prokoski et al. | 382/2 |
| 5,262,647 | 11/1993 | Kumada | 250/351 |

FOREIGN PATENT DOCUMENTS

| | | |
|---|---|---|
| 874865-A | 7/1979 | Belgium. |
| 854384 | 10/1970 | Canada. |
| 1141211 | 2/1983 | Canada. |
| 1196086 | 10/1985 | Canada. |
| 1283476 | 4/1991 | Canada. |
| 2072174 | 12/1992 | Canada. |

OTHER PUBLICATIONS

Fiala, S. et al, "Infrared Scanning of Cattle and Swine" Can. J. of Anim. Sci. 63: 1008 (1983).

Hurnik, J. F. et al, "Detection of Health Disorders in Dairy Cattle Utilizing a Thermal Infrared Scanning Technique"; Can. J. of Anim. Sci. 64; 1071–1073 (Dec. 1984).

Vaden, M. F. et al, "Thermography: A Technique for Subclinical Diagnosis of Osteoarthritis", Am. J. Vet. Res., vol. 41, No. 8 (Aug., 1980).

Purohit, R. C. et al, "Thermography in the Diagnosis of Inflammatory Processes in the Horse", Am. J. Vet. Res., vol, No. 8 (Aug. 1980).

Purohit, R. C. et al, "Thermography of the Bovine Scrotum", Am. J. Vet. Res., vol. 46, No. 11 (Nov. 1985); 2388–2392.

Hurnik, J. F. et al., "An Investigation of Skin Temperature Differentials in Relation to Estrus in Dairy Cattle Using a Thermal Infrared Scanning Technique" J. Anim. Sci. vol. 61, No. 5, (1985) pp. 1095–1102.

Braverman, Y., "Potential of Infrared Thermography for the Detection of Summer Seasonal Recurrent Dermatitis (Sweet Itch In Horses", Veterinary Record (1989) 125:372–374.

Turner, T. P. et al, "Thermography: A Review In Equine Medicine", Compendium Equine, Nov., 1986, pp. 855–861.

Purohit, R. C. et al, "Thermographic Diagnosis of Horner's Syndrome in the Horse", Am. J. Vet. Res., vol. 41, No. 8: 1180–1182.

(List continued on next page.)

*Primary Examiner*—Max Hindenburg
*Attorney, Agent, or Firm*—Merchant, Gould, Smith, Edell, Welter & Schmidt

[57] ABSTRACT

The invention provides a method and apparatus for remote sensing of livestock, using a thermographic image sensing system, in order to determine one or more of the number, weight, location, temperature, carcass pH, etc., of animals in a surveillance area. A thermographic image comprising pixels of the area is sent to a digitizing board in a microcomputer, where the image is converted into a number array. The numbers are then interpreted by software to provide the desired information in a decipherable form.

29 Claims, 4 Drawing Sheets

OTHER PUBLICATIONS

Shuran, M. et al, "Quantitation of Energy Expenditure by Infrared Thermography", Am. J. Clin. Nutr. 1991:53:1361-7.

Gearheart, W. W. et al, "Infrared Thermography of Pigs With Known Genotypes for Stress Susceptability in Relation to Pork Quality", Can. J. Anim. Sci. 69:491-495 (Jun. 1989).

Pick, M. "Erste Ergebnisse . . . Infrarottermographen" Tierärztl. Prax. 12, 229-238 (1984) [English summary attached].

Minagawa, H. et al, "Measurement of Pigs' Weights by an Image Analysis", Paper No. 927023, presented at 1992 (21-24 Jun., 1992) International Summer Meeting of The American Society of Agricultural Engineers.

"Piggeries Look to hi-tech future", Hog Quarterly, Fall 1992, p. 43.

"Defensive Driving" (Gary Stix), Scientific American, Sep. 92, p. 164-B.

Gariepy, C. et al., "Ante-Mortem Detection of PSE and DFD by Infrared Thermography of Pigs Before Stunning", Meat Science 25 (1989) 37-41.

Schofield, C. P. et al., "Image Analysis for Estimating the Weight of Live Animals", SPIE vol. 1379 Optics in Agriculture (1990) 209-219.

Schofield, C. P. "Evaluation of Image Analysis as a Means of Estimating the Weight of Pigs", J. Agric. Engng Res. (1990) 47: 287-296.

ANALYSIS OF VARIANCE F = 2.13 (p = 0.049)

REMOTE THERMOGRAPHIC SENSING OF LIVESTOCK

The present invention relates to a method and apparatus for the remote sensing of animals using thermographic sensing technology and computer software for analysis and presentation of thermographic data obtained.

Currently in agriculture there are some bottlenecks that impede further advances in production efficiency and animal health and welfare. Growth monitoring is currently done using inventory analysis and physical weighing of animals. These procedures are invasive (ie. disrupt the everyday life and growth of the livestock), labour intensive, and phone to human error. Advances in growth monitoring would enhance our knowledge of animal production, and would allow producers in the field to identify inefficiency in their operations.

A second major bottleneck is the identification of animals which develop diseases that reduce growth and performance. Currently disease diagnosis depends primarily on human recognition of the signs. This recognition is limited by the experience and ability of the person examining the animal and be time-and-labour allotted to screening for disease.

Livestock production would be enhanced if current technology could be refined to do some of the above tasks, eg. with instruments that would remotely sense farm animals and determine their quantity, location, temperature and body mass. Such could be applied to livestock production where accurate animal inventories and daily growth rates are difficult to obtain. Pig farms estimate growth rates over the marketing period (6 months). Poultry farms monitor growth by weighing a random subset of birds on a regular basis. Beef feedlots spend a lot of time and money examining incoming cattle for respiratory disease. Any advances in automating these processes would be extremely useful. Large swine operations have inventories of many thousands of animals. Any technology that would enhance the monitoring of animals would also be welcomed by the industry.

With the advent of efficient microprocessor technology, remote sensing of objects has been developed for commercial manufacturing processes. Using mechanical and electronic means of determining characteristics such as size, shape, colour, texture, etc. allows for less dependence on human input, and ultimately leads to more efficient handling and processing methods. In some cases, remote sensing and measuring can add a level of precision beyond human capability.

Precise measurements of animals are desired in many livestock operations in order to monitor production. For example, the weight and temperature of animals are important in assessing production rates, presence of disease, environmental conditions etc. In using traditional techniques, obtaining such measurements involves handling animals individually, which can be manually demanding and time consuming. Ideally, a method of obtaining such measurements remotely, ie. without manually handling each animal individually, and readily upon the demand of a livestock operation worker, would be substantially beneficial.

We have now found a method and apparatus that can bet teed for remotely sensing animals, in one aspect, a livestock operation and to provide for example, weight and temperature data on demand, or continuously if desired. These rely in part on thermographic sensing technology. Thermographic technology has been adapted for many temperature sensing purposes, eg. in medicine for detecting inflammation or other pathological conditions of humans, as disclosed in U.S. Pat. No. 5,056,525. It has also been used in the diagnosis of pathological conditions in animals, as exemplified in the paper: Hurnik, J. F., De Boer, S., and Webster, A. B., Detection of Health Disorders in Dairy Cattle Utilizing a Thermal Infrared Scanning Technique, Can. J. Anim. Sci. 64: 1071–1073, However, such and other uses to date have been for the analysis of specific animals under specific care or attention, and not performed remotely on animals on a surveillance or continuous basis.

SUMMARY OF THE INVENTION

The invention provides an apparatus for remote sensing of information about an animal in an area and making said information available to a person in a decipherable form. The information may be production information about livestock, or health status information of animals in a zoo, for example. The apparatus in a broad aspect comprises a means for remotely obtaining a thermographic image of the area, which image can be used directly or indirectly to provide an absolute or relative temperature of an animal in the area. There is also a means for converting the image into computer readable form, a means for interpreting that form to provide the information, and a means for displaying the information in a person-decipherable form, eg. in a form with meaning to a livestock manager or zoo-keeper.

The means for converting the image into computer readable form preferably includes a means for converting the image into a number array, each number having a position corresponding to a pixel in the image and a value corresponding to a relative brightness of the pixel. This may be accomplished on a video-digitizer circuit board.

Preferably, the means for remotely obtaining the thermographic image of the area is a thermographic imaging camera. The camera is preferably mountable on a means for moving the camera from over one area to another, so that animals in different areas may be viewed selectively. The means for moving the camera preferably includes a track, extending over two or more different areas. The camera is preferably slideably mounted on the track.

In another referred embodiment of the apparatus using a thermographic imaging camera, the camera is fixable to view only one area, eg. a temporary holding pen for animals for slaughter. Livestock in such area would be changed regularly, so a fixed camera would be sufficient in such context.

The means for interpreting the computer readable form to provide the information preferably includes processing means for segmenting a group of pixels associated with an animal in the area from pixels associated with background and applying a unique identifier to the animal profile. The processing means also preferably includes one or more of the following: means for segmenting a single group of pixels associated with a plurality of animals and determining an approximation of a number of animals associated with the single group of pixels; means for counting the unique identifier and the approximation of a number of animals associated with the single group of pixels to determine an estimate of a number of animals in the area; means for counting a total number of pixels in an animal profile to determine an approximate weight of an associated animal in the area; means for determining a centre of an animal from locations of all pixels in an associated animal profile and then determining an approximate position of the animal in the area; means for determining an approximate absolute or relative temperature of an animal in the area based on average brightness of pixels in an associated animal profile; means for determining an estimate of carcass 24 hour pH from the approximate (pixel) temperature variation of an animal before slaughter; means for determining an estimate of visual PSE meat score from the approximate (pixel) temperature of an animal before slaughter; and means for determining an approximate absolute or relative temperature of background to animals in the area based on average brightness of pixels in the background.

In another aspect there is provided a method of remotely sensing information about an animal in an area, which comprises obtaining a thermographic image of the area, wherein the image directly or indirectly is able to provide an absolute or relative temperature of an animal in the area, converting the image into computer readable form, interpreting the form to provide the information, and displaying the information in a person-decipherable form.

BRIEF DESCRIPTION OF THE DRAWINGS

In the accompanying drawings which illustrate preferred embodiments of the present invention.

DETAILED DESCRIPTION OF PREFERRED EMBODIMENTS

Figure 1:
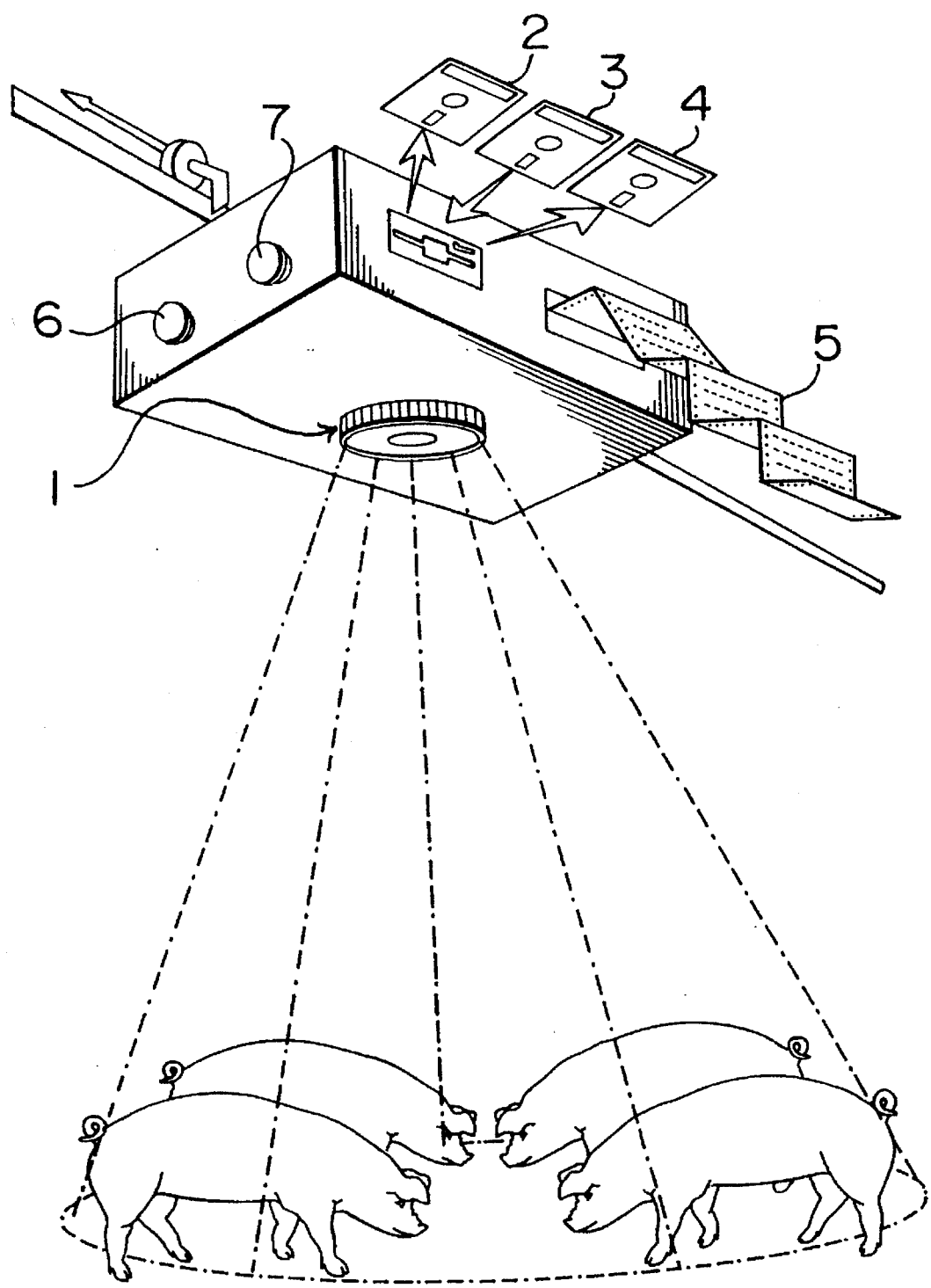
FIG. 1 is a perspective view of an apparatus, according to the present invention, in use in monitoring pigs.

We have developed a method for the remote sensing of animals using a thermographic image sensing system. The method involves sensing the presence of animals, the biomass (number and weight of animals) and temperature of the animals (which is an indicator of the health of the animals). The method is free of human contact or intervention with the animals, and in this sense is "remote". The information sensed by the sensing system is tabulated and conveyed to a human, eg. on a chart, printout or computer screen.

The thermographic image sensing system uses a thermographic camera which sends a video image to a digitizing board in a microcomputer. Software interprets the following features of the video image: number of animals in the area imaged; mass (estimated weight) of the animals; average skin temperature of each animal; approximate location of the animals in the imaged area; and the temperature of the surfaces adjoining the location of the animals. The software delivers the above information in a decipherable manner to those gathering information about the animals. Such information is relayed by diskette, wire or infrared transmission from the camera/digitizing board combination to another computer that is operated by an "animal handler".

Under the present method, the thermographic screening of livestock before slaughter enables operators of the method to recognize animal health and quality problems while the animal is still alive and/or immediately after slaughter. Thermography detects changes in the body surface temperature as an indication of the metabolic state of the animal. Current non-thermographic methods obtain metabolic status information using invasive, labour dependant, time consuming techniques. The present method, sometimes referred to as "Remote Thermographic Animal Sensing" or "RTAS", allows for automated screening of animals for example, on a farm, or in an abattoir.

Using RTAS, the following conditions are detectable: general body infections or infections to anatomical regions of an animal; injuries to, or bruising of an animal; metabolic disorders such as exhaustion or exertion (eg. Porcine Stress Syndrome (PSS) which can cause pork carcass quality problems such as P.S.E.—Pale Soft Exudative meat condition). Other benefits of using RTAS include: labour savings to the slaughter and meat processing industries through an automated process for activities currently carried out manually and visually; improved selection and separation of animals having ideal metabolic status, thereby making the slaughter process more efficient and streamlined; identification of problem animals allows for useful interventions to occur while the animal is alive—eg. an exhausted animal may be rested, or an excited or nervous animal can be allowed to calm down and cool off, or an animal with PSS can be rested which is known to result in improved pork quality; identification of infected animals will allow for removal of those animals for a detailed inspection before slaughter occurs, thereby reducing the risk of disease in consumers, so there is an improvement in food safety and the inspection process is enhanced.

The thermographic sensing system used in the present method requires a thermographic imaging means, eg. camera, that can alone or with an adjunct, provide absolute or relative temperatures of objects in the field of view of the means. We selected a camera available through the company ISI Group Inc. of 211 Conchas S.E., Albuquerque, N.M., U.S.A., namely Model 9100, which operates under pyroelectric vidicon technology and produces a US Standard RS-170 output (30 frames per second). Since this camera does not provide absolute temperatures, but rather only thermographic images, the images produced required calibration to enable relative temperatures and ultimately absolute temperatures to be obtained. Our selected camera required very slight movement to produce a scanned image of the infrared scene.

The microcomputer for selection preferably has the following specifications: 486/33, or faster, central processing unit; 200 Mb, or higher, hard disk; 10–20 Mb, or higher, ram; ISA bus architecture (due to the selected digitizing board's AT specifications). A digitizing board and software were used to capture and interconnect the imaging camera with the microcomputer and software programs. We selected a Matrox Model IP-8 digitizing board, supplied by Matrox Electronic Systems Ltd. of Dorval, Quebec, Canada, which provides a resolution of 512×512×8 bits, accepts RS-170 input, has a 2 Mb video frame buffer on the card, connects to an ISA bus, and has an extensive library of software development tools and demonstration programs for directly accessing the frame buffers.

Image analysis in the present method is a set of procedures for enhancing the visibility of objects in a scene, separating "objects of interest" ie. animals, from "background" and performing measurements on the objects of interest and, optionally, the background. The scene sensed by the thermographic camera produces a signal which is conducted to a video-digitizer circuit board installed in the microcomputer. The board converts the signal into a square array of numbers inside the computer. The position of a number in the array corresponds to the position of one picture dot, or "pixel", in the scene. The value of the number indicates the pixel's "brightness".

The number of pixels in the array determines the resolution of the image. Usually the size of these arrays is 256-rows by 256-columns (more than 65,000 pixels) and may be as large as 1024-rows by 1024-columns (over one million pixels). We used a 512×480 size of array in out tests. The pixel values typically range from 0 to 255. The large size of the data array, combined with the intensive computations done on them, preferably requires computer hardware that can perform extremely fast and contain very large amounts of pixel data. Otherwise the time needed to extract information from a scene becomes excessive.

We used a pen with pigs to develop the present method and apparatus (see FIG. 1). FIG. 1 illustrates a camera 1, start button 6, stop button 7, pen data disk 2, parameters disk 3, error trace disk 4 and printed reports 5. The thermographic camera was placed above the pen, pointing downwards, so that only the tops of pigs were visible to the camera. Data of interest for collection included the positions, sizes and temperatures of individual pigs. Computer algorithms for resolving these from the scene were developed and included adjusting for poor contrast between pigs and background, and compensating for overlapping images of pigs, eg. images formed from two or more pigs in substantial contact with each other.

Figure 4:
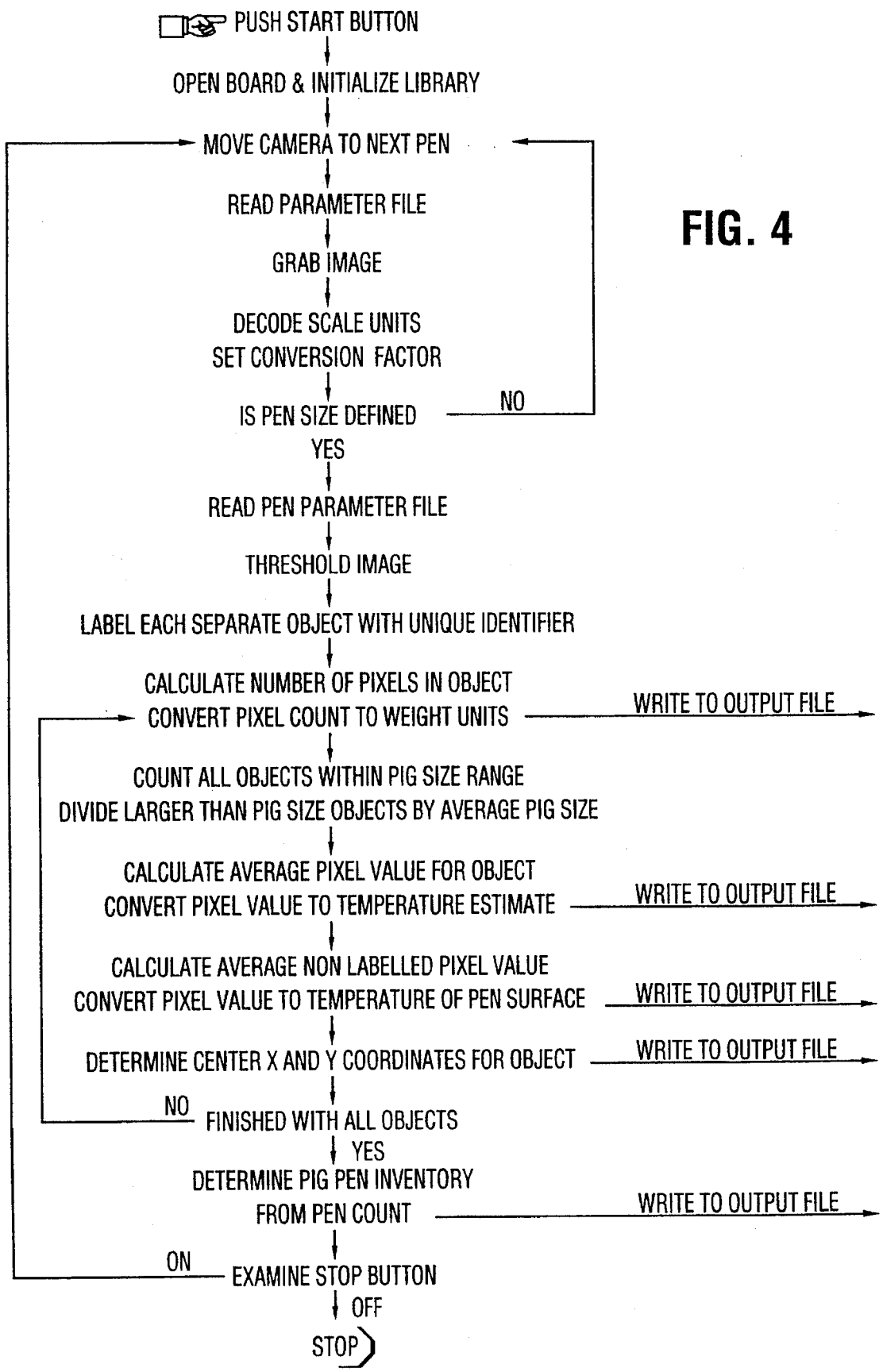
FIG. 4 is a flow chart of one example of basic thermographic sensing operations that may be employed under the present invention.

FIG. 4 illustrates a flowchart for software designed for use in our remote animal sensing technology. It will be apparent to any person skilled in the art that other software designs may also be used in accordance with the scope of the present invention, so references to the software in FIG. 4 are non-limiting.

In one commercial application of the apparatus of the present invention the camera is designed to move mechanically from animal pen to animal pen. In another application the camera may remain stationary as animals move below and through the field of view. In either case, the first step in the image analysis is to obtain a video frame from the thermographic camera, wherein the frame includes animal images of animals within a predefined field of view. In our tests the frame was captured as a 512×480 pixel array. The array is then "cleaned" through an erode and dilate process. The array next undergoes a threshold process to define the animal profiles and separate them from the background "non-animal" areas. A row by row method utilizing a fixed formula may be used, as may a method of choosing the threshold by a dip in the histogram that is found at the transition between animal and background pixel values. In some cases further refinements in choosing the threshold value can come from a method of evaluating the image array and choosing the pixel value where the background begins to break up, thereby eliminating the background and not eroding any animal pixels. The final thresholding method may be any one of the above methods either alone or in combination, and is not limited to the described methods, in keeping with the scope of the present invention.

The thresholded image contains defined animal areas which are labelled and analyzed. Objects smaller than a predefined animal area are discarded; objects within an anticipated size are counted; and objects larger than the predetermined size are divided by the predefined size to estimate the number of animals in large objects. The latter technique compensates for situations where the animals are so close together that the software perceives them as one animal. The parameter file which contains pen specific information is used to determine the predetermined animal size. The parameter file is initialized whenever the apparatus encounters the pen for the first time. The number of estimated animals is written to the output file, as is the estimation of the temperature of each animal based on the pixel values. The temperature may be in absolute form, ie. °C., if the camera is calibrated against an object of known temperature on a regular basis. A relative determination of the temperature may also be incorporated by noting which animals in each pen have an elevated temperature compared to their pen mates (see Table VII).

An average of the non-animal pixel values represents the background pen temperatures. These are written to the output file either in absolute or relative form.

The X and Y coordinates of the centre of each object will give the location of each animal and this information is then written to the output file.

The output file information is processed by a database management program to deliver information to the livestock operator in a useful manner. Inventory information can provide an estimate of the total animal inventory. Warning indicators can notify the livestock operator if significant changes in inventory are found. Animal weight data can be used to provide growth rate estimates for each pen of animals. Warning indicators can notify the operator if the animals are not growing at the optimal rates or if the animals are about to reach market weights. The disease incidence rate can be reported for each pen by noting the number of animals with elevated temperatures (fevers), again warning indicators can alert the livestock operator of disease outbreaks and which pens are affected. The location and background information can be plotted in graphic form to allow the producer to view the locations of the animals and remotely view the temperature status of the pens. Warning indicators can draw the operator's attention to pens which are abnormally cold or hot.

Figure 5:
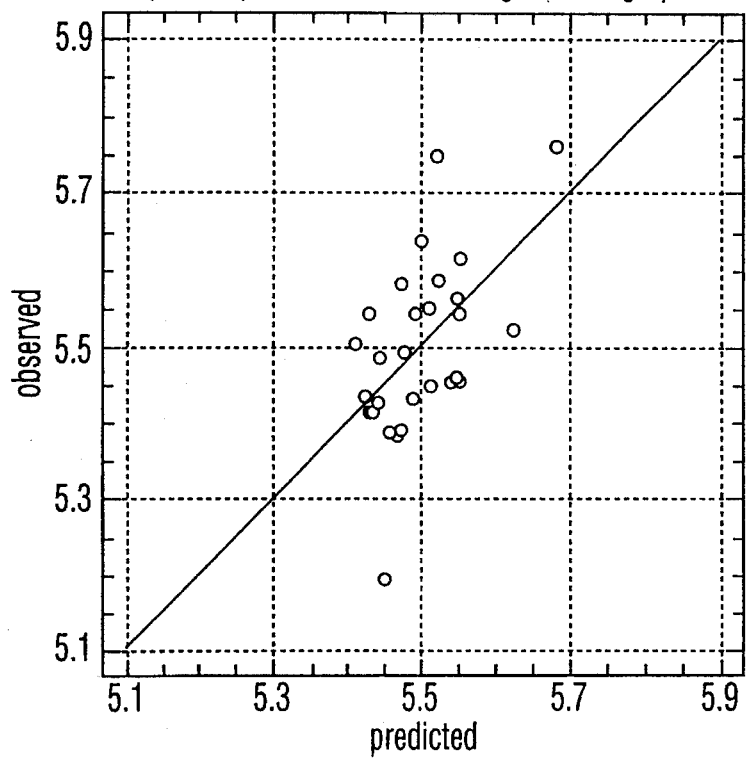
FIG. 5 is a graph of actual vs pixel carcass pH in a study of applying the present invention to pigs.

Our work has also established a link between thermographic remote sensing of pigs prior to slaughter and subsequent carcass meat quality. Carcass 24 hour pH and visual PSE meat score can be predicted from temperature data obtained under the present invention. With respect to pH, it is the case that the pH of pork 24 hours after slaughter is a criterion of meat quality. We have found that animals with a large variation in pixel values are associated with an increased muscle pH (see FIG. 5). This relationship is strengthened when looking at pigs within on farm source. The significance of this finding is that commercial abattoirs may be able to sort loads of pigs on arrival into those that will give the highest quality pork.

Figure 6:
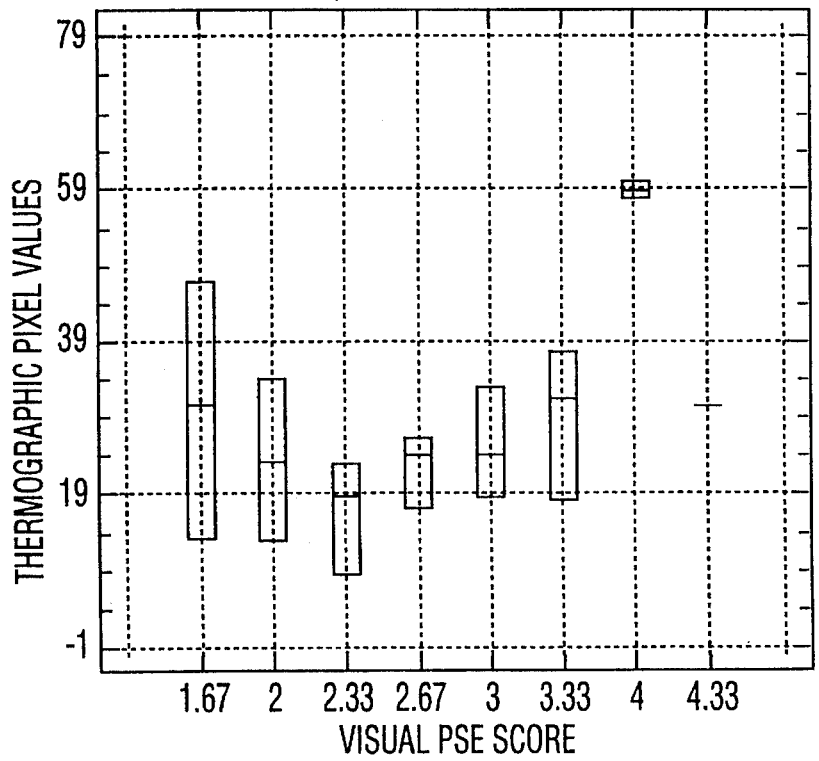
FIG. 6 is a graph of PSE (Pale Soft Exudative meat) score vs pixel temperature in a study of applying the present invention to pigs.

The PSE condition of pork is a major quality flaw resulting in significant marketing losses. Thermographic sensing of pigs prior to slaughter has revealed a relationship between PSE pork and the thermographic pixel values (see FIG. 6). Pigs with higher pixel values tend to have an elevated PSE score, particularly when the score is greater than 2. Detecting PSE problems prior to slaughter can allow for quality selection when sorting live pigs and diverting PSE pigs to a rest facility where the pigs can rest and reduce the incidence of PSE pork.

In summary of some of the preferred aspects of one embodiment of the present invention, separating "pig" pixels into individual pigs involves scanning the image row-by-row starting from the top; when a pig profile is encountered, it is labelled with a unique identifier. Scanning continues until every pig profile has been filled with a unique identifier. Compensation for overlapping pig profiles is made. Once labelled, the unique identifiers and the pixels for each unique identifier may be used to determine one or more of the following:

Numbers: The unique identifiers yield an approximation of the number of pigs in the pen;

Weights: A count of the number of pixels in each unique identifier yields a measurement of the mass of the pig;

Positions: Calculating the center for each identifier yields where the pigs are positioned in the pen;

Temperatures: Averaging the brightness of the pixels associated with each identifier yields a measure of the pig's body temperature. Pixel temperature can be used to predict actual carcass 24 hour pH and visual PSE meat score; and Background: Averaging the brightness of the pixels not associated with any identifier, ie. of the "non-pig" pixels, approximates the background (pen) temperature.

There may be other useful kinds of information that can be obtained from the thermographic image data, as may occur to someone skilled in the art from consideration of the present description, so the above list is not intended to be limiting.

The following Tables I–III illustrate a Parameter File layout and a sample Parameter File which have been developed for use in preferred software for carrying out the method and apparatus of the subject invention.

TABLE I

Parameter File Layout

| KEYWORD | DEFAULT VALUE | ACCEPTED VALUES |
|---|---|---|
| Barn-Name = | blank | one-line phrase to identify/describe the barn; used as a title on any printouts |
| Barn-ID = | 'BARN' | 4 character mnemonic uniquely identifying this barn location |
| Barn-Temp-MAX = | 15 | Range for 'background' barn temperatures |
| Barn-Temp-MIN = | 10 | |
| Species = | Porcine | Porcine, Bovine, etc . . . |
| Shipping-Weight = | 102 | target shipping weight (see Weight-Units) |
| Normal-Body-Temp = | 39 | normal average body temperature (see Temp-Units) |
| Temp-Units = | C | units of measure for all TEMPERATURE measurments; C-celsius; F-fahrenheit; K-kelvin |
| Distance-Units = | M | units of measure for all DISTANCE measurements, R-screen rastor units-, MM-millimeters; CM-centimeters; M-meters; IN-inches, FT-feet; YD-yards |
| Weight-Units = | KG | units of measure for all WEIGHT measurements, GM-grams, KG-kilograms, OZ-ounces, LB-pounds |
| Lens = | 18 mm | lens installed in camera |
| Output-Filename = | Cymmddhh.mm$^2$ | 8 character file name AND 3 character file extension to identify the barn DATA file: |
| Printing = | S | D(etails only) S(ummaries only) or B(oth): indicates whether a printout is required; necessitates a painting device being correctly attached |

TABLE II

| KEYWORD | DEFAULT VALUE | ACCEPTED VALUES |
|---|---|---|
| | | The following parameters are repented for each pen. |
| Pen-Width = | 20 | width of the pen (see Distance-Units) |
| Pen-Length = | 20 | length of the pen (see Distance-Units) |
| Pen-Camera-Height = | 10 | height of camera above the pen (see Distance-Units) |
| Pen-Avg-Weight | | average weight of an animal to be housed in this pen; used to 'separate' overlapping images when performing the inventory counting |
| Pen-MAX-Temp = | | Range for average animal body temperature in this pen |
| Pen-MIN-Temp = | | |
| Pen-MAX-Weight = | | Range for average animal body weight in this pen |
| Pen-MIN-Weight = | | |
| Pen-ID = | A(8) | 8-characters of alpha-numerics labelling each pen in the order they are 'seen'; upon reading this parameter, the program pauses until 'signalled' to proceed; |

TABLE III

Sample Parameter File

Barn-Name = Swineman, Joe
Barn-ID = JOES
Species = PORCINE
Shipping-Weight = 85
Normal-Body-Temp = 39
Temp-Units = C
Distance-Units = FT
Weight-Units = KG
Lens = 18
Output-Filename = SWINEMAN.JOE
Printing = Y
Pen-Width = 17.5
Pen-Length = 15.3
Pen-Camera-Height = 12.3
Pen-ID = 002
Pen-Width = 14.4

TABLE III-continued

Sample Parameter File

Pen-Length = 18.75
Pen-Camera-Height = 12.3
Pen-ID = 001
Pen-Width = 15.25
Pen-Length = 15.75
Pen-Camera-Height = 14.75
Pen-ID = 004
Pen-Width = 18.8
Pen-Length = 20.25
Pen-Camera-Height = 14.75
Pen-ID = 003

Table IV below illustrates an output data file in ASCII text, one row per animal per pen, columnar data:

TABLE IV

| Col. | Size | Field | Format | Description |
|---|---|---|---|---|
| 1 | 4 | BarnID | A(4) | |
| 2 | 8 | PenNum | A(8) | |
| 3 | 6 | Date | 999999 | YYMMDD |
| 4 | 4 | Time | 9999 | HHMM |
| 5 | 3 | AnimNum | 999 | 1–999 |
| 6 | 6 | EstWeight | 9999.9 | 0–9999.9 |
| 7 | 2 | WeightUnits | AA | GM,KG,OZ,LB |
| 8 | 5 | AvgTemp | 999.9 | 0–999.9 |
| 9 | 1 | TempUnits | A | C,F,K |
| 10 | 9 | Xcenter. | 9999.9 | 0–9999.9 |
| 11 | 6 | Ycenter | 9999.9 | 0–9999.9 |
| 12 | 2 | CenterUnits | Ah | R,MM,CM,M,IN,FT |
| 13 | 5 | OrientAng | 999.9 | 0–360 DEGREES |

58 + 12 separators = 70 bytes

Example Output DATA File

```
Col.    1      1    2    2    3    3    4    4    5    5    6    6    7
 5      0      5    0    5    0    5    0    5    0    5    0    5    0

MACD  PEN4AB-2  921203  1418  001  0025.6  KG  038.9  C  0012.5  0007.2  FT  025.7
MACD  PEN4AB-2  921203  1418  002  0023.2  KG  039.4  C  0002.3  0003.5  FT  215.3
MACD  PEN4AB-2  921203  1418  003  0022.3  KG  037.2  C  0004.5  0002.4  FT  035.2
MACD  PEN4AB-2  921203  1418  004  0024.4  KG  038.3  C  0013.7  0005.2  FT  145.4
MACD  PEN4AB-2  921203  1418  005  0021.6  KG  039.1  C  0011.4  0006.3  FT  075.5
  :       :       :      :    :      :    :    :    :    :      :     :    :.... Orient Ang
  :       :       :      :    :      :    :    :    :    :      :     :.... Center Units
  :       :       :      :    :      :    :    :    :    :      :.... Y Center
  :       :       :      :    :      :    :    :    :    :.... X Center
  :       :       :      :    :      :    :    :    :.... Temp Units
  :       :       :      :    :      :    :    :.... Avg Temp
  :       :       :      :    :      :    :.... Weight Units
  :       :       :      :    :      :.... Est Weight
  :       :       :      :    :.... Anim Num
  :       :       :      :.... Time
  :       :       :.... Date
  :       :.... Pen Num
  :.... Barn ID
```

Table V below illustrates Field Definitions developed for use in preferred software for use in carrying out the method and apparatus of the subject invention:

TABLE V

Field Definitions

| | |
|---|---|
| 1. Barn 10 | Barn Identification: 4-character mnemonic to identify the barn in which the following pens are located |
| 2. Pen Num | Pen Number identification label assigned to uniquely |

TABLE V-continued

Field Definitions

|  |  |
|---|---|
|  | identify each pen; obtained from Parameter File |
| 3. Date | Date: format YYMMDD; eg. 921203 is Dec. 3, 1992 |
| 4. Time | Time of Day: 24-hour clock; format HHMM; eg. 2143 is 21 hours and 43 minutes (ie. 9:43pm) |
| 5. Anim Num | Animal Number: sequential number counting each labelled image; this is not an animal identification number but rather a sequential count of the numbers of animals in the pen |
| 6. Est Weight | Estimated Weight: |
| 7. Weight Units | Units for Estimated Weight: GM = grams, KG = kilograms, OZ = ounces, LB = pounds |
| 8. Avg Temp | Average Temperature: |
| 9. Temp Units | Units for Average Temperature: C = Celsius, F = Fahrenheit, K = Kelvin |
| 10. X center | X coordinate for Center of Gravity |
| 11. Y center | Y coordinate for Center of Gravity |
| 12. Center Units | Units for Center of Gravity: same units for both X and Y coordinates; R = rastor, MM = millimeters, CM = centimeters, M = meters, IN = inches, FT = feet |
| 13. Orient Ang | Angle of Orientation: units are "degrees" of rotation from zero; zero is pointing to right or image screen |

Table VI below illustrates a typical Pen Details Report that may be printed at the end of each pen, ie. as an available report layout under operation of the preferred software. This "ticker tape" type of report would provide immediate feedback and information to the herdsman or farm manager, eg. while the unit is proceeding through a barn. The latter example anticipates that the camera would be on an overhead guide or track and could be selectively moved from one area for surveillance to another.

TABLE VI

Pen Details Report
Much like a "cash register" receipt, and printed at the end of each pen, this ticker tape report will provide immediate feedback and information to the herdsman or farm manager WHILE the unit is procceding through the barn.
PEN DETAILS Barn-Name: Swineman, Joe  Species: PORCINE
Lens: 10 mm  **Shipping-Weight: 105KG
File: SWINEMAN.JOE  *Normal-Body-Temp: 39 C.

| # | Weight | Temp. | X-Location-Y | Angle | Temp | Weight |
|---|---|---|---|---|---|---|

Pen = PEN2AB-2  W × L = 17.5 ft × 15.3 ft
12-Mar-94 9:34 pm  25 Animals: HiTemp = 3, ShipWt = 4
 Camera at 12.3 ft H

| 001 | 25.6 kg | 38.9 C. | 12.5 ft | 7.2 ft | 25.7 |  |
| 002 | 23.2 kg | 39.4 C. | 2.3 ft | 3.5 ft | 215.3 | T |
|  |  | : |  |  |  |  |
| 024 | 24.4 kg | 38.3 C. | 13.7 ft | 5.2 ft | 145.4 |  |
| 023 | 21.6 kg | 39.1 C. | 11.4 ft | 6.3 ft | 75.5 | T |

PEN = PEN2AB-1  W × L = 14.4 ft × 18.8 ft
12-Mar-94 9:39 pm  15 Animals: HiTemp = 2, ShipWt = 5
 Camera at 12.3 ft H

| 001 | 85.6 kg | 38.3 C. | 12.5 ft | 7.2 ft | 25.7 | W |
| 002 | 73.2 kg | 39.4 C. | 2.3 ft | 3.5 ft | 215.3 | T |
|  |  | : |  |  |  |  |
| 014 | 84.4 kg | 39.3 C. | 13.7 ft | 5.2 ft | 145.4 |  |
| 015 | 81.6 kg | 39.1 C. | 11.4 ft | 6.3 ft | 75.5 | T |

PEN = PEN2AB-4  W × L = 15.3 ft × 15.8 ft
12-Mar-94 9:44 pm  13 Animals: HiTemp = 0, ShipWt = 2
 Camera at 14.8 ft H

| 001 | 95.6 kg | 38.9 C. | 12.5 ft | 7.2 ft | 25.7 | W |
| 002 | 83.2 kg | 38.4 C. | 2.3 ft | 3:5 ft | 215.3 |  |
|  |  | : |  |  |  |  |

TABLE VI-continued

Pen Details Report
Much like a "cash register" receipt, and printed at the end of each pen, this ticker tape report will provide immediate feedback and information to the herdsman or farm manager WHILE the unit is procceding through the barn.
PEN DETAILS

| 012 | 84.4 kg | 30.3 C. | 13.7 ft | 5.2 ft | 145.4 |  |
| 013 | 81.6 kg | 39.1 C. | 11.4 ft | 6.3 ft | 75.5 |  |

Pen = PEN2AB-3  W × L = 18.8 ft × 20.3 ft
12-Mar-94 9:49 pm  19 Animals: HiTemp = 1, ShipWt = 0
 Camera at 14.8 ft H

| 001 | 35.6 kg | 38.9 C. | 12.5 ft | 7.2 ft | 25.7 |  |
| 002 | 43.2 kg | 37.4 C. | 2.3 ft | 3.5 ft | 215.3 |  |
|  |  | : |  |  |  |  |
| 018 | 44.4 kg | 33.3 C. | 13.7 ft | 5.2 ft | 145.4 |  |
| 019 | 31.6 kg | 39.1 C. | 11.4 ft | 6.3 ft | 75.5 | T |

Table VII below illustrates a Summary Report that may be printed at the end of the entire circuit of pens. The livestock manager can therefore be provided with a condensed, pen-based, inventory showing total numbers of pigs: in each pen; their temperatures; and, their weights for comparison to desired shipping weights for example.

TABLE VII

SUMMARY

Barn-Name: Swineman, Joe  Species: PORCINE
Lens: 18 mm  **Shipping-Weight: 105KG
File: SWINEMAN.JOE  *Normal-Body-Temp: 39 C.

| March 12, 1998 Time | Pen | # with HiTemp | # at ShipWt | Total # in Pen |
|---|---|---|---|---|
| 9:34pm | PEN2AB-2 | 3 | 4 | 25 |
| 9:39pm | PEN2AB-1 | 2 | 5 | 15 |
| 9:44pm | PEN2AB-4 | 0 | 2 | 13 |
| 9:49pm | PEN2AB-3 | 1 | 0 | 19 |
| : |  |  |  |  |

The preferable external interface for the processed data under the present method and apparatus is the data set of pen-based observations. This interface could also be achieved by a removable floppy diskette for transporting the data set(s) to a microcomputer for use in the database management program. It is also contemplated that the data set could be transmitted in other ways such as wireless modem or hardwired asynchronous communications line.

Figure 2:
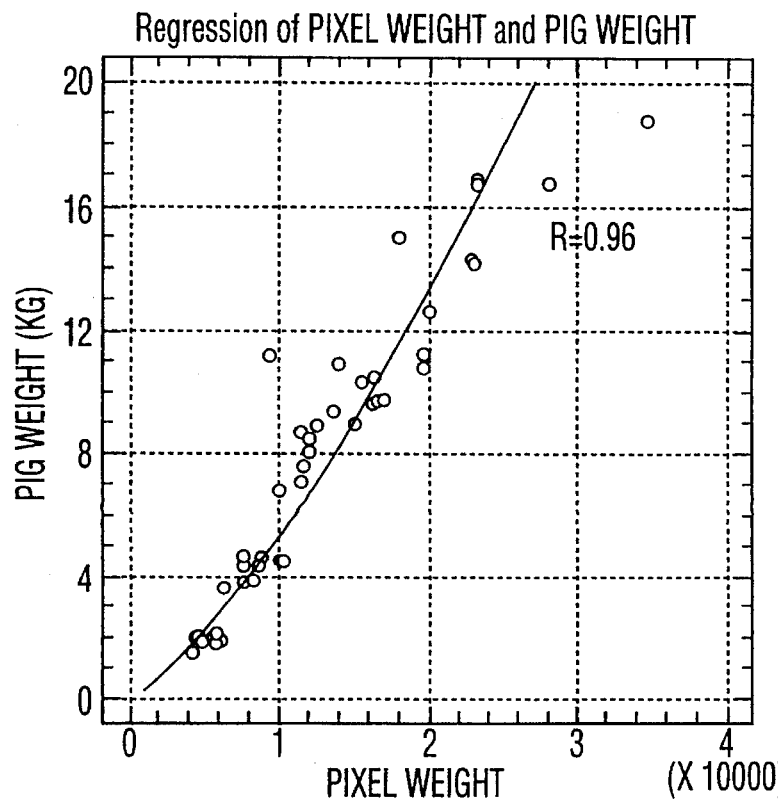
FIG. 2 is a graph of actual weight (scale weight) various pigs vs pixel weight (weight determined from pixel values obtained by thermographic image analysis) in a study of applying the present invention to pigs.
Figure 3:
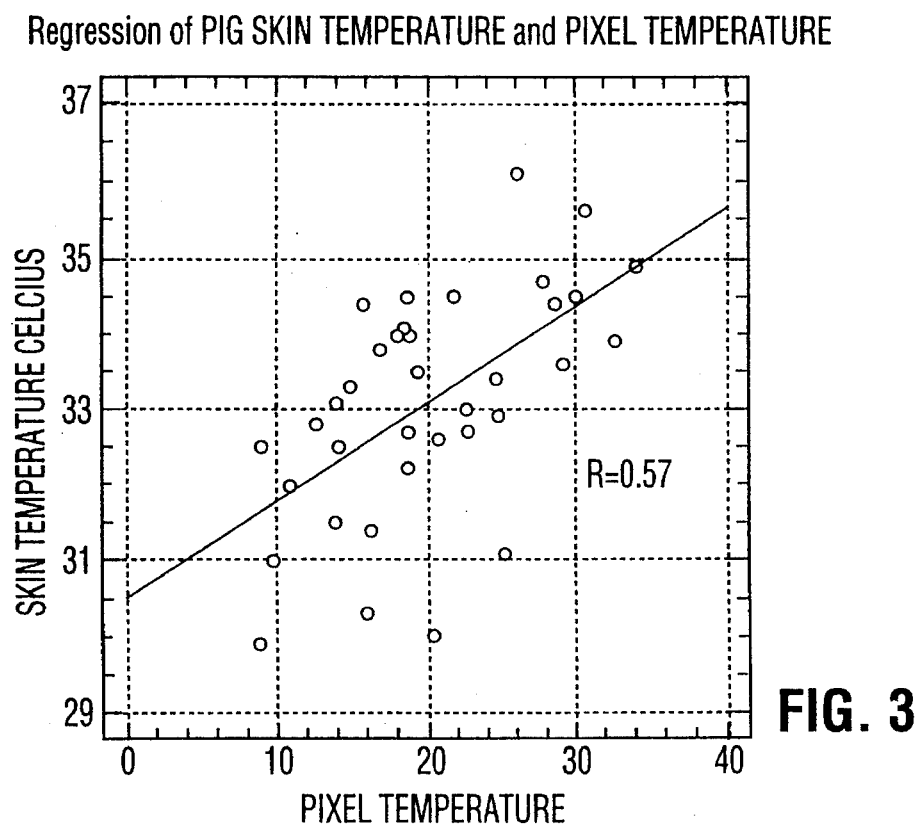
FIG. 3 is a graph of actual skin temperature of various pigs vs pixel temperature (temperature determined from pixel values obtained by thermographic image analysis) in a study of applying the present invention to pigs.

FIG. 2 indicates that estimating the weight of pigs under the present method has been achieved in our experiments. Plotting actual weight (scale weight—Y axis) vs pixel value (X axis) shows a strong, useful relationship exists. Although less data is available for correlating average pixel brightness to actual pig temperature, FIG. 3 does establish that a useful relationship exists between such data and that broad estimates of an animal's temperature can be measured remotely. Our tests also indicate that thermographic remote sensing appears to be able to predict pig carcass pH, as shown in Table VIII below and in FIG. 5.

TABLE VIII

Model Fitting results for: Carcass pH

| INDEPENDENT VARIABLE | COEFFICIENT | STD. ERROR | T-VALUE | SIG. LEVEL |
| --- | --- | --- | --- | --- |
| CONSTANT | 5.340569 | 0.054929 | 97.22 | 0.0000 |
| THERMOGRAPHIC VARIABLE | 0.012696 | 0.005319 | 2.3872 | 0.0249 |
| FAM VARIABLE | 0.0026292 | 0.001159 | 2.3228 | 0.0286 |

R-SQ. (ADJ.) = 0.2434  SE = 0.099753  MAE = 0.074226  DurbWat = 1.972
28 observations fitted, forecast(s) computed for 61 missing val. of dep. var.

Analysis of Variance for the Full Regression

| Source | Sum of Squares | DF | Mean Square | F-Ratio | P-value |
| --- | --- | --- | --- | --- | --- |
| Model | 0.106316 | 2 | 0.0531582 | 5.34218 | .0117 |
| Error | 0.248767 | 25 | 0.00995066 | | |
| Total (Corr.) | 0.355083 | 27 | | | |

R-squared = 0.299413  Stnd. error of est. = 0.099753
R-squared (Adj. for d.i.) = 0.243366  Durbin-Watson statistic = 1.97219

We have made studies of the possible financial benefits of the present method and apparatus to swine farming, which are summarized as follows:

a. Reduced mortality rate: By allowing earlier diagnosis of diseases in a finishing barn, a reduction in mortality should result. Current average mortality is 3–4%. It should be possible to reduce this to a level of 1.5–2% by early diagnosis and treatment. This reduction of mortality rate will reduce the cost of production per pig of $2.00 to $2.50 per pig. For a 100 sow pig farm, this yields an annual saving of $4000–$5000.

b. Fewer "poor growing" pigs: Improvements in health will improve growth rates on pig farms. It will also reduce the number of chronic "poor growing" pigs which impair overall growth on pig fame. By reducing the number of "poor growing" pigs, the "average days to market" number will drop. A modest improvement, such as 5 days less to market, will reduce costs by $2.50 per pig.

c. Improved days-to-market: By being able to monitor growth accurately, producers will be able to identify weak areas in pig growth, and to correct them. A modest improvement in days-to-market on average farms (5 days) will reduce cost a further $2.00–$2.50 per pig.

d. Less time looking for market-weight pigs: The concept of being able to monitor pig growth will allow farmers to identify pigs that are market weight. This will reduce the amount of time spent looking for market weight pigs. On a 100 sow farm, two hours per week could be saved, which would translate into a $1000 saving per year (or $1.00 per pig).

It will be obvious to one skilled in the art that modifications to the specific examples used for illustration may be made without departing from the spirit and scope of this invention.

What is claimed is:

1. An apparatus for remote sensing of weight information about an animal in an area and making said information available in a decipherable form to an observer, comprising:

means without human operation for remotely obtaining a thermographic image of the area, which image can be used directly or indirectly to provide a weight of an animal in the area;

means for converting maid image into computer readable form;

means for interpreting said form to provide said information; and means for displaying said information in a decipherable form to said observer.

2. An apparatus as defined in claim 1, wherein the means for remotely obtaining a thermographic image of the area is a thermographic imaging camera, and said image consists of pixels.

3. An apparatus as defined in claim 1, wherein said image comprises pixels, said means for converting said image into computer readable, form includes means for converting said pixels into a number array, each said number having a position corresponding to a pixel in said image and each said number having a value corresponding to a relative brightness of said pixel.

4. An apparatus as defined in claim 3, wherein said means for converting said image into computer readable form includes a video-digitizer circuit board.

5. An apparatus as defined in claim 2, wherein said camera is mountable on a means for moving said camera over said area and at least one other area for selective remote sensing of an animal in said area or said at least one other area.

6. An apparatus as defined in claim 5, wherein said means for moving the camera includes a track, extending from over said area to said at least one other area, and on which said camera is slideably mounted.

7. An apparatus as defined in claim 2, wherein said camera is fixable to view only said area.

8. An apparatus as defined in claim 3, wherein said means for interpreting said form to provide said information includes processing means for segmenting a group of pixels associated with said animal from pixels associated with background thereby providing an animal profile of said animal, and applying a unique identifier to said animal profile.

9. An apparatus as defined in claim 8 wherein said processing means also includes means for segmenting a single group of pixels associated with a plurality of animals in said area and determining an approximation of a number of animals associated with said single group of pixels.

10. An apparatus as defined in claim 9 wherein said processing means includes means for counting said unique identifier and said approximation of a number of animals associated with said single group of pixels, to determine an estimate of a number of animals in the area.

11. An apparatus as defined in claim 8 wherein said processing means includes means for counting a total number of pixels in said animal profile to determine an approximate weight of said animal.

12. An apparatus as defined in claim 8 wherein said processing means includes means for determining a centre of said animal from locations of all pixels in said animal profile and then determining an approximate position of said animal in the area.

13. An apparatus as defined in claim 8 wherein said processing means includes means for determining an approximate absolute or relative temperature of said animal based on average brightness of pixels in said animal profile.

14. An apparatus as defined in claim 13 wherein said processing means also includes means for determining from said approximate temperature prior to slaughter of said animal, an approximation of carcass pH twenty-four hours after slaughter.

15. An apparatus as defined in claim 13 wherein said processing means also includes means for determining from said approximate temperature prior to slaughter of said animal, an approximation of post-slaughter visual Pale Soft Exudative meat score.

16. An apparatus as defined in claim 8, wherein said processing means includes means for determining an approximate absolute or relative temperature of said background based on average brightness of said pixels associated with background.

17. A method of remotely sensing weight information about an animal in an area, which comprises:
obtaining, without human operation, a thermographic image of the area, wherein the image can be used to provide a weight of an animal in the area;
converting said image into computer readable form;
interpreting said form to provide said information; and
displaying said information in a decipherable form to a human observer.

18. A method as defined in claim 17, wherein the thermographic image is provided by a thermographic imaging camera.

19. A method as defined in claim 17, wherein the camera is fixed over the area for obtaining information about an animal in the area at one time and another animal in the area at a different time.

20. A method as defined in claim 17, wherein the camera is moveable to at least one other area for obtaining information about an animal in said other area.

21. A method as defined in claim 17, wherein said interpreting includes segmenting a group of pixels associated with an animal in the area from pixels associated with background thereby providing an animal profile of said animal, and applying a unique identifier to said animal profile.

22. A method as defined in claim 21 wherein said interpreting also includes segmenting a single group of pixels associated with a plurality of animals and determining an approximation of a number of animals associated with said single group of pixels.

23. A method as defined in claim 22, wherein said interpreting also includes counting said unique identifier and said approximation of a number of animals associated with said single group of pixels, to determine an estimate of a number of animals in the area.

24. A method as defined in claim 21, wherein said interpreting also includes counting a total number of pixels in said animal profile to determine an approximate weight of said animal.

25. A method as defined in claim 21, wherein said interpreting also includes determining a centre of said animal from locations of all pixels in said animal profile and then determining an approximate position of the animal in the area.

26. A method as defined in claim 21, wherein said interpreting also includes determining an approximate absolute or relative temperature of said animal based on average brightness of pixels in said animal profile.

27. A method as defined in claim 21, wherein said interpreting includes determining an approximate absolute or relative temperature of said background based on average brightness of said pixels associated with background.

28. A method as defined in claim 26, wherein said interpreting includes determining from said approximate temperature, prior to slaughter of an animal, an approximation of carcass pH twenty-four hours after slaughter.

29. A method as defined in claim 26, wherein said interpreting includes determining from said approximate temperature, prior to slaughter of an animal, an approximation of post-slaughter visual Pale Soft Exudative meat score.

* * * * *